United States Patent
Dwivedi et al.

(10) Patent No.: US 9,708,300 B2
(45) Date of Patent: Jul. 18, 2017

(54) AMORPHOUS FORM OF VILAZODONE HYDROCHLORIDE AND PROCESS FOR ITS PREPARATION

(75) Inventors: Shirprakash Dhar Dwivedi, Ahmedabad (IN); Ramesh Chandra Singh, Ahmedabad (IN); Jigar Mukundbhai Raval, Ahmedabad (IN)

(73) Assignee: Cadila Healthcare Limited, Ahmedabad (IN)

( * ) Notice: Subject to any disclaimer, the term of this patent is extended or adjusted under 35 U.S.C. 154(b) by 616 days.

(21) Appl. No.: 14/006,016

(22) PCT Filed: Mar. 16, 2012

(86) PCT No.: PCT/IN2012/000182
§ 371 (c)(1),
(2), (4) Date: Nov. 18, 2013

(87) PCT Pub. No.: WO2012/131706
PCT Pub. Date: Oct. 4, 2012

(65) Prior Publication Data
US 2014/0057925 A1   Feb. 27, 2014

(30) Foreign Application Priority Data
Mar. 20, 2011 (IN) .......................... 167/MUM/2011

(51) Int. Cl.
*A61K 31/404* (2006.01)
*C07D 405/12* (2006.01)

(52) U.S. Cl.
CPC .......... *C07D 405/12* (2013.01); *A61K 31/404* (2013.01)

(58) Field of Classification Search
CPC ........................... C07D 405/12; A61K 31/404
See application file for complete search history.

(56) References Cited

U.S. PATENT DOCUMENTS

| 3,609,152 A | * | 9/1971 | Hess | C07D 491/04 540/600 |
| 4,337,341 A | * | 6/1982 | Zimmerman | C07C 45/68 546/112 |
| 7,381,726 B2 | * | 6/2008 | Bathe | A61K 31/496 514/252.1 |
| 7,834,020 B2 | * | 11/2010 | Bathe | A61K 31/496 514/254.09 |
| 2004/0147528 A1 | | 7/2004 | Bathe et al. | |
| 2009/0023749 A1 | | 1/2009 | Bathe et al. | |
| 2010/0016332 A1 | | 1/2010 | Bathe et al. | |
| 2011/0183994 A1 | | 7/2011 | Bathe et al. | |
| 2011/0190317 A1 | | 8/2011 | Bathe et al. | |
| 2011/0294824 A1 | | 12/2011 | Bathe et al. | |
| 2011/0294825 A1 | | 12/2011 | Bathe et al. | |
| 2011/0312971 A1 | | 12/2011 | Bathe et al. | |

FOREIGN PATENT DOCUMENTS

WO   WO 02/102794   12/2002

OTHER PUBLICATIONS

Written Opinion of the ISA for PCT/IN2012/000182, four pages, dated Aug. 21, 2012.
International Preliminary Report on Patentability for PCT/IN2012/000182, five pages, dated Sep. 24, 2013.
International Search Report for PCT/IN2012/000182 mailed Aug. 21, 2012.

* cited by examiner

*Primary Examiner* — Alexander R Pagano
*Assistant Examiner* — Ebenezer O Sackey
(74) *Attorney, Agent, or Firm* — Nixon & Vanderhye P.C.

(57) ABSTRACT

The present invention relates to an amorphous form of vilazodone hydrochloride and process for the preparation of amorphous form of vilazodone hydrochloride. The invention also relates to pharmaceutical compositions that include a therapeutically effective amount of the amorphous form of vilazodone hydrochloride and use of said compositions for the treatment of major depressive disorder (MDD).

36 Claims, 2 Drawing Sheets

AMORPHOUS FORM OF VILAZODONE HYDROCHLORIDE AND PROCESS FOR ITS PREPARATION

Figure 1:
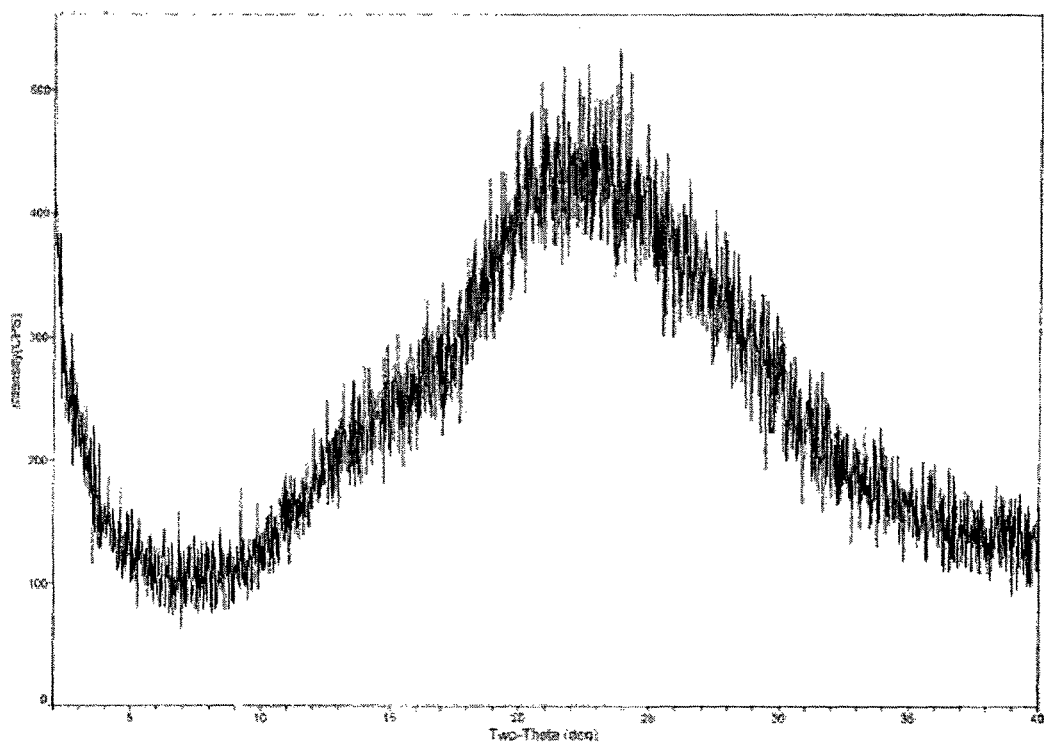

This application is the U.S. national phase of International Application No. PCT/IN2012/000182 filed 16 Mar. 2012 which designated the U.S. and claims priority to IN 167/MUM/2011 filed 20 Mar. 2011, the entire contents of each of which are hereby incorporated by reference.

FIELD OF THE INVENTION

The invention relates to an amorphous form of vilazodone hydrochloride, and to a process for the preparation of amorphous form of vilazodone hydrochloride. The invention also relates to pharmaceutical compositions that include a therapeutically effective amount of the amorphous form of vilazodone hydrochloride, and use of said compositions for the treatment of major depressive disorder (MDD).

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Vilazodone i.e. 1-[4-(5-cyanoindol-3-yl)butyl]-4-(2-carbamoyl-benzofuran-5-yl)-piperazine, and physiologically acceptable salts thereof, are disclosed in U.S. Pat. No. 5,532,241. PCT International Publication No. WO 00/72832 discloses use of Vilazodone in treating certain medical disorders.

U.S. Pat. Nos. 7,834,020 B2 and 7,381,726 B2 disclose fifteen crystalline forms of vilazodone hydrochloride designated as Form-I through Form-XV. They also disclose an amorphous type Form-XVI, which is not a pure amorphous form as it contains characteristic two theta peaks pertaining to crystalline nature of the form. Hence, the art does not provide a pure amorphous form of vilazodone hydrochloride.

The present invention provides substantially pure amorphous form of vilazodone hydrochloride having polymorphic purity greater than 99.9% with no detectable amount of any crystalline forms.

dissolution characteristics and in some cases different bioavailability patterns compared to the crystalline form (Econno T., Chem. Pharm. Bull., 1990; 38: 2003-2007). For some therapeutic indications, one bioavailability pattern may be favoured over another.

Amorphous forms of some drugs exhibit much higher bioavailability than the crystalline forms, which leads to the selection of the amorphous form as the final drug substance for pharmaceutical dosage from development. Additionally, the aqueous solubility of crystalline form is lower than of amorphous form in some drugs, which may result in the difference in their in vivo bioavailability. Therefore, it is desirable to have amorphous forms of drugs with high purity to meet the needs of regulatory agencies and also highly reproducible process for their preparation.

In view of the above, it is also desirable to provide an efficient, economical and eco-friendly process for the preparation of highly pure vilazodone hydrochloride in amorphous form.

OBJECTS OF THE INVENTION

It is an important object of the present invention to provide an amorphous form of vilazodone hydrochloride.

Another object of the present invention is to provide substantially pure amorphous form of vilazodone hydrochloride having high polymorphic purity.

It is another object of the present invention is to provide a process for preparing the amorphous form of vilazodone hydrochloride.

It is another object of the present invention to provide compositions comprising the amorphous form of vilazodone hydrochloride substantially free of one or more of its corresponding impurities.

It is another object of the present invention to provide a pharmaceutical composition comprising the stable amorphous form of vilazodone hydrochloride together with one or more pharmaceutically acceptable carriers, excipients or diluents.

SUMMARY OF THE INVENTION

The above and other objects of the present invention are achieved by providing an amorphous form of vilazodone hydrochloride of Formula (I).

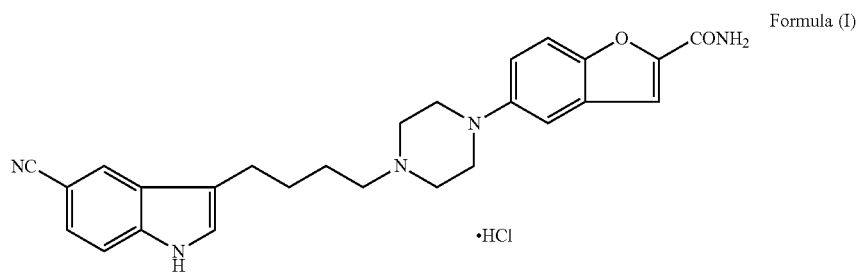 [SMILES: N#Cc1ccc2[nH]cc(CCCCN3CCN(c4ccc5oc(C(N)=O)cc5c4)CC3)c2c1 ; Cl]

Formula (I)

Figure 2:
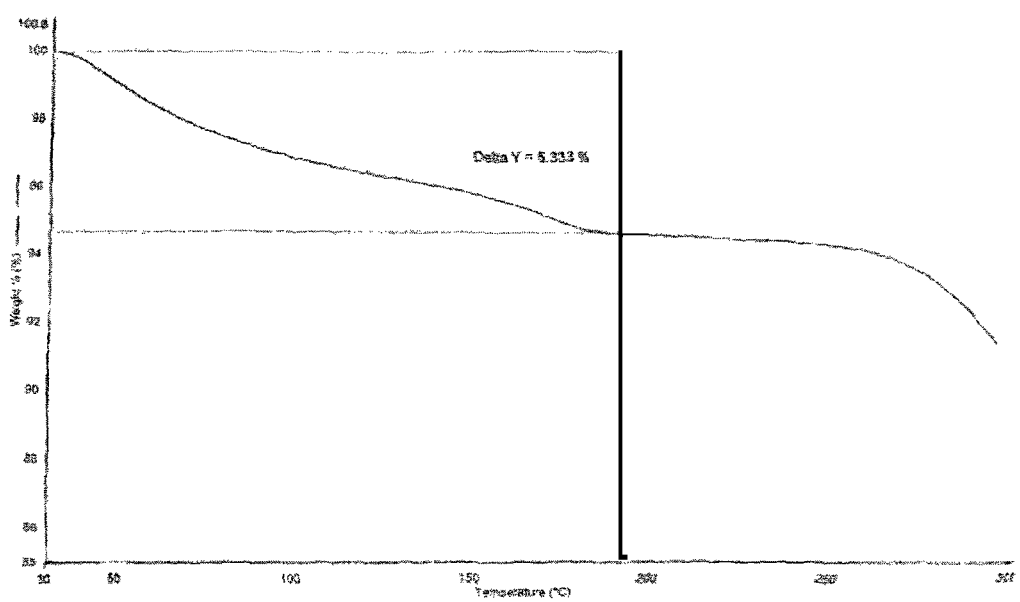

Crystalline solids normally require a significant amount of energy for dissolution due to their highly organized lattice like structures. For example, the energy required for a drug molecule to escape from a crystal is more than from an amorphous or a non-crystalline form. It is known that the amorphous forms in a number of drugs exhibit different The amorphous form of vilazodone hydrochloride can have the X-ray powder diffraction as depicted in FIG. 1 and the TGA graph as depicted in FIG. 2.

The present invention also discloses a process for the preparation of the amorphous form of vilazodone hydrochloride.

The present invention discloses a substantially pure amorphous form of vilazodone hydrochloride having polymorphic purity greater than 90%. It can provide the amorphous form of vilazodone hydrochloride having less than 10% of crystalline vilazodone hydrochloride, preferably less than 5%. It can also provide amorphous form of vilazodone hydrochloride having less than 1% of crystalline vilazodone hydrochloride, for example with no detectable amount of any crystalline forms.

In another embodiment of the present invention there is provided an amorphous form of vilazodone hydrochloride having water content of from about 0.5% to about 10% wt/wt.

In another embodiment of the present invention there is provided a process for the preparation of the amorphous form of vilazodone hydrochloride. The process includes providing a solution of vilazodone hydrochloride in one or more solvents; and recovering the amorphous form of vilazodone hydrochloride from the solution thereof by the removal of the solvent.

Removing the solvent may include one or more of distillation, distillation under vacuum, evaporation, spray drying, freeze drying, filtration, decantation, and centrifugation. The amorphous form of vilazodone hydrochloride may be recovered from the solution by spray drying. Alternatively, the vilazodone hydrochloride in an amorphous form may be recovered from the solution by freeze drying. The process may include further forming the product so obtained into a finished dosage form.

The amorphous form of vilazodone hydrochloride can also be recovered from the solution by adding a suitable anti-solvent resulting in the precipitation of the amorphous form and removing the solvent therefrom by filtration, decantation or centrifugation. The anti-solvent may be selected from a group of solvents in which vilazodone hydrochloride is insoluble or poorly soluble or partially soluble and is known to a person of ordinary skill in the art.

In another embodiment of the present invention there is provided an amorphous form of vilazodone hydrochloride, substantially free from residual organic solvents.

In yet another embodiment of the present invention there is provided a stable amorphous form of vilazodone hydrochloride thereof, which is stable during storage and drying.

In a further embodiment of the present invention there are provided storage and packaging conditions for the amorphous form of vilazodone hydrochloride.

In further embodiment of the present invention there is provided an amorphous form of vilazodone hydrochloride having particle size distribution wherein the 10th volume percentile particle size (D10) is less than about 50 µm, the 50th volume percentile particle size (D50) is less than about 200 µm, the 90th volume percentile particle size (D90) is less than about 400 µm, or any combination thereof.

In another embodiment of the present invention there is provided an amorphous form of vilazodone hydrochloride having particle size in terms of d95, is preferably less than about 100 microns, more preferably less than about 50 microns and most preferably less than about 30 microns. As used throughout the disclosure, the term d95 means that 95% of the particles (based on volume) are smaller than or equal to the indicated size.

In another aspect there is provided a process for the preparation of the amorphous form of vilazodone hydrochloride having particle size in terms of D95 less than about 100 microns.

In another embodiment of the present invention there is provided an amorphous form of vilazodone hydrochloride having purity of greater than about 95%, or greater than about 98%, or greater than about 99%, or greater than about 99.5%, or greater than about 99.8%, or greater than about 99.9%, as determined by using high performance liquid chromatography (HPLC).

In another embodiment of the present invention, there are provided compositions comprising amorphous form of vilazodone hydrochloride substantially free of one or more of its corresponding impurities as measured by HPLC.

In another embodiment of the present invention, there is provided a pharmaceutical composition comprising the stable amorphous form of vilazodone hydrochloride together with one or more pharmaceutically acceptable carriers, excipients or diluents.

In a further embodiment of the present invention there is provided a pharmaceutical composition comprising the stabilized amorphous solid dispersion of vilazodone hydrochloride together with one or more pharmaceutically acceptable carriers, optionally with one or more pharmaceutically acceptable excipients.

BRIEF DESCRIPTION OF THE ACCOMPANYING DRAWINGS

FIG. 1. shows X-ray diffractogram (XRD) of amorphous form of vilazodone hydrochloride.

FIG. 2. shows thermal gravimetric analysis (TGA) of amorphous form of vilazodone hydrochloride.

DETAILED DESCRIPTION OF THE INVENTION

As used herein, the terms "suspending", "slurrying" and "triturating" are interchangeable, and refer to a process carried out in a heterogeneous mixture where complete dissolution does not occur. Also, heating the suspension or slurry can result in a homogenous mixture where complete or partial dissolution occurs at an elevated temperature or ambient temperature.

The term "elevated temperature" used herein means heating the reaction mixture, either heterogeneous or homogeneous, at a temperature from about 35° C. to boiling point of solvent, for example from about 35° C. to about 100° C. The term "ambient temperature" used herein means slurrying the reaction mixture, either heterogeneous or homogeneous, at a temperature from about 10° C. to about 35° C. of solvent.

As used herein, the terms "obtaining" means isolating the amorphous form of vilazodone hydrochloride by way of filtration, filtration under vacuum, centrifugation, decantation and the like. The product obtained may be further or additionally dried to achieve the desired moisture values. For example, the product may be dried in a tray drier, dried under vacuum and/or in a Fluid Bed Drier.

As used herein, the term "storage stable" includes the amorphous form of vilazodone hydrochloride after exposure to a relative humidity of 75% at 40° C. or relative humidity of 60% at 25° C., for a period of at least three months shows no change in the polymorphic form by X-ray powder diffraction. "Suitable solvent" means a single or a combination of two or more solvents.

As used herein, the term "substantially pure amorphous form" of vilazodone hydrochloride represents polymorphic purity of amorphous form of vilazodone hydrochloride greater than 90%. The amorphous form may not show any detectable amount of any other crystalline forms as determined by using X-ray powder diffraction pattern (XRD).

The present invention discloses an amorphous form of vilazodone hydrochloride having purity of greater than about 95%, or greater than about 98%, or greater than about 99%, or greater than about 99.5%, or greater than about 99.8%, or greater than about 99.9%, as determined using high performance liquid chromatography (HPLC).

In one aspect there is provided an amorphous form of vilazodone hydrochloride. In another aspect there is provided a substantially pure amorphous form of vilazodone hydrochloride.

In another aspect, there is provided a process for the preparation of the amorphous form of vilazodone hydrochloride thereof without simultaneous formation of crystalline forms or which will enable the conversion of crystalline forms into the amorphous from.

In one aspect there is provided a process for preparation of the amorphous form of vilazodone hydrochloride, the process comprises the steps of:
a) providing a solution of vilazodone hydrochloride in one or more solvents; and
b) recovering the amorphous form of vilazodone hydrochloride from the solution thereof by the removal of the solvents.

Suitable solvents that may be used include but are not limited to water; alcohols such as methanol, ethanol, isopropanol, 2-propanol, 1-butanol, t-butyl alcohol, 1-pentanol, 2-pentanol, amyl alcohol, ethylene glycol, glycerol and the like; ketones such as acetone, butanone, 2-pentanone, 3-pentanone, methyl butyl ketone, methyl isobutyl ketone, and the like; esters such as ethyl formate, methyl acetate, ethyl acetate, propyl acetate, t-butyl acetate, isobutyl acetate, hydrocarbons like toluene, xylene, methylene dichloride, ethylene dichloride, chlorobenzene, and the like, nitriles like acetonitrile, ethers like diethyl ether, diisopropyl ether, t-butyl methyl ether, dibutyl ether, tetrahydrofuran, 1,4-dioxane, 2-methoxy ethanol, polar aprotic solvents like N,N-dimethylformamide, N,N-dimethyl acetamide, N-methylpyrrolidone, pyridine, dimethylsulfoxide, sulfolane, formamide, acetamide, propanamide, pyridine and the like; and mixtures thereof.

The amorphous form of the vilazodone hydrochloride may be recovered from the solution by removing the solvent. Suitable techniques which may be used for the removal of solvent include using a rotational distillation device such as a Buchi Rotavapor, spray drying, agitated thin film drying ("ATFD"), freeze drying (lyophilization), and the like or any other suitable technique.

The present invention discloses a process for the preparation of amorphous form of vilazodone hydrochloride, which includes one or more of the following steps:
a) providing a solution of vilazodone hydrochloride in one or more solvents;
b) adding a suitable anti-solvent; and
c) isolating the amorphous form of vilazodone hydrochloride.

The solution of vilazodone hydrochloride can be obtained by the known methods that include direct use of a reaction mixture containing vilazodone hydrochloride that is obtained in the course of its synthesis, or dissolving vilazodone hydrochloride in a suitable solvent or mixture of solvents.

Suitable solvents may include but are not limited to water; alcohols such as methanol, ethanol, isopropanol, 2-propanol, 1-butanol, t-butyl alcohol, 1-pentanol, 2-pentanol, amyl alcohol, ethylene glycol, glycerol and the like; ketones such as acetone, butanone, 2-pentanone, 3-pentanone, methyl butyl ketone, methyl isobutyl ketone, and the like; esters such as ethyl formate, methyl acetate, ethyl acetate, propyl acetate, t-butyl acetate, isobutyl acetate, hydrocarbons like toluene, xylene, methylene dichloride, ethylene dichloride, chlorobenzene, and the like, nitriles like acetonitrile, ethers like diethyl ether, diisopropyl ether, t-butyl methyl ether, dibutyl ether, tetrahydrofuran, 1,4-dioxane, 2-methoxyethanol, polar aprotic solvents like N,N-dimethylformamide, N,N-dimethylacetamide, N-methylpyrrolidone, pyridine, dimethylsulfoxide, sulfolane, formamide, acetamide, propanamide, pyridine, and the like; and mixtures thereof.

Suitable anti-solvents may include one or more of hydrocarbons like hexanes, n-heptane, n-pentane, cyclohexane, methylcyclohexane and the like; aromatic hydrocarbons like toluene, xylene, chlorobenzene, ethylbenzene and the like; ethers like diethyl ether, diisopropyl ether, t-butyl methyl ether, dibutyl ether, tetrahydrofuran, 1,4-dioxane, 2-methoxyethanol, and the like.

The amorphous form of vilazodone hydrochloride may be isolated by removing the solvents. Suitable techniques which may be used for the removal of solvent include using a rotational distillation device such as a Buchi Rotavapor, spray drying, agitated thin film drying ("ATFD"), freeze drying (lyophilization), and the like or any other suitable technique.

In particular, the solvent may be removed by a spray drying technique. The technique includes spray drying a solution of vilazodone hydrochloride and involves the spray drying of feed stock, which is prepared as mentioned below. The feedstock may be dozed into the spray-drying instrument JISL Mini Spray-drier LSD-48 and spray drying may be carried out under the following parameters. The feedstock for spray drying may be a clear solution or in dispersion form.

| Sr. No | Parameters | Conditions |
|---|---|---|
| a) | Feed pump | 10-50 rpm |
| b) | Inlet temperature | 35°-80° C. |
| c) | Outlet temperature | 30°-60° C. |
| d) | Aspirator rate | 1000-1500 rpm |
| e) | Vacuum for conveying the dry product | 30-120 mm of Hg |
| f) | Hot air supply | 2-4 Kg/cm$^2$ |
| g) | Atomizer Speed: | 40,000-100,000 rpm |

In another preferred embodiment, the spray drying of vilazodone hydrochloride may be performed by a) maintaining the feed rate of the feed stock at 50-250 ml/hr, preferably 100-200 ml/hr; b) maintaining the inlet temperature in the range of 35° C.-80° C., preferably, 50° C.-70° C.; c) maintaining the aspirator rate between 1000-1500 rpm, preferably 1200-1400 rpm; d) maintaining the outlet temperature in the range of 30° C. to 60° C., preferably, 40° C. to 50° C.; e) maintaining air flow at 2-4 Kg/cm, preferably 2 Kg/cm; f) maintaining Atomizer speed between 20,000-100,000 rpm, preferably, 40,000-50,000 rpm, and; g) maintaining the vacuum at 30-120 mm of Hg, preferably 50-80 mm of Hg.

The feed stock of vilazodone hydrochloride was conveniently prepared by dissolving a wet cake of vilazodone hydrochloride in a solvent selected from the group of solvents, for example acetone, $C_{1-4}$ alcohol, $C_{2-6}$ acetate, acetonitrile, methylene dichloride, water or mixture thereof; most preferably water, methanol, ethanol, acetone, ethyl acetate, methylene dichloride, water-methanol or water-ethanol, water-acetone are suitable solvent used or such solvents that evaporate easily to afford dry product, most preferably acetone, methanol, ethanol, ethyl acetate or mixtures of the above.

In another aspect there is provided the amorphous form of vilazodone hydrochloride having water content from about 0.5% to about 10% wt/wt.

In another aspect there is provided the amorphous form of vilazodone hydrochloride is substantially free from of residual organic solvents.

According to a further embodiment, vilazodone hydrochloride can be spray dried by dissolving or suspending or slurring in suitable solvent or solvent-water system to get amorphous form. In the present invention feed stock of Vilazodone Hydrochloride in water, solvent or aqueous solvent system is spray-dried. Thus obtain spry-dried compound is in amorphous form, this fact is again confirmed by the X-ray powder diffractogram of spray-dried vilazodone hydrochloride.

In a preferred embodiment of the invention, weighed quantity of vilazodone hydrochloride is dissolved in 2-10 volumes of chosen solvent, preferably 4-5 volumes solvent at 25° C. to 30° C. The content is stirred for 30 minutes at 25° C. to 30° C. The content is filtered through Hyflosupercell, and filtrate is spray dried under following conditions. The obtained powder is further dried at 40° C. for 12-16 hours under vacuum to afford the stable amorphous form of vilazodone hydrochloride.

The present invention provides a process for the preparation of the amorphous form of vilazodone hydrochloride, substantially free from residual organic solvents. The process includes:

a) providing vilazodone hydrochloride having less than 10% residual organic solvent;
b) triturating vilazodone hydrochloride in water, or contacting vilazodone hydrochloride with humid air in a fluidized bed drier, or drying vilazodone hydrochloride under reduced pressure of less than about 30 mmHg at less than 60° C.;
c) optionally micronizing vilazodone hydrochloride; and
d) drying the product obtain in step c) to obtain the amorphous form of vilazodone hydrochloride substantially free of residual organic solvents.

In another aspect the invention provides the amorphous form of vilazodone hydrochloride having particle size distributions wherein the 10th volume percentile particle size (D10) is less than about 50 µm, the 50th volume percentile particle size (D50) is less than about 200 µm, or the 90th volume percentile particle size (D90) is less than about 400 µm, or any combination thereof.

In another aspect there is provided the amorphous form of vilazodone hydrochloride having particle size in terms of d95, is preferably less than about 100 microns, more preferably less than about 50 microns and most preferably less than about 30 microns. As used throughout the disclosure, the term d95 means that 95% of the particles (based on volume) are smaller than or equal to the indicated size.

In another aspect there is provided a process for preparing amorphous form of vilazodone hydrochloride having particle size in terms of d95 less than about 100 microns.

In another aspect there is provided a process for preparing amorphous vilazodone hydrochloride having particle size in terms of d95 less than about 100 microns, comprising the steps of;
(a) milling amorphous vilazodone hydrochloride,
(b) slurrying micronized vilazodone hydrochloride in one or more organic solvents to form a solution;
(c) isolating amorphous form of vilazodone hydrochloride having particle size in terms of d95 less than about 100 microns.

The milling off vilazodone hydrochloride in step (a) is performed with feeding pressure of about 3 kg and grinding pressure of about 4 kg.

The suitable solvent for step (b) is selected from group consisting of $C_{3-6}$ ketones, water, N-methylpyrrolidone, $C_{3-6}$ amides, halo-substituted $C_{6-12}$ aromatic hydrocarbons, propylene glycol, dimethyl sulfoxide, dimethyl carbonate, $C_{1-8}$ alkyl alcohols, acetonitrile $C_{2-6}$ alkyl acetates, cellosolve, dimethyl carbonate, polyethylene glycol methyl ether and $C_{2-8}$ ethers.

In another aspect, there is provided a table amorphous form of vilazodone hydrochloride, which is stable during storage and drying.

The stable amorphous form of vilazodone hydrochloride, is stored under nitrogen atmosphere and packed in a double polythene bag tied with a thread, keeping primary packing containing amorphous vilazodone hydrochloride or salts thereof inside a black color polyethylene bag containing oxygen busters and sealing it, placing above the double polyethylene bag inside a triple laminated bag optionally containing oxygen busters and sealing it, and placing the sealed triple laminated bag inside a closed high density polyethylene (HDPE) container and storing in controlled environment chamber at about 25° C. and/or 40° C.

In another aspect, the present invention provides the amorphous form of vilazodone hydrochloride of formula (I) having purity of greater than about 90%, or greater than about 95%, or greater than about 98%, or greater than about 99%, or greater than about 99.5%, or greater than about 99.8%, or greater than about 99.9%, as determined using high performance liquid chromatography (HPLC).

The present invention also discloses compositions comprising the amorphous vilazodone hydrochloride substantially free of one or more of its corresponding impurities as measured by HPLC.

In another aspect, there is provided amorphous vilazodone or salts thereof having particle size distributions wherein the 10th volume percentile particle size (D10) is less than about 50 µm, the 50th volume percentile particle size (D50) is less than about 200 µm, or the 90th volume percentile particle size (D90) is less than about 400 µm, or any combination thereof.

Powder X-ray Diffraction of amorphous form of vilazodone hydrochloride can be obtained under following conditions.

(i) Characterization by Powder X-Ray Diffraction

The X-ray powder diffraction spectrum was measured under the following experimental conditions:
Instrument: X-Ray Diffractometer, D/Max-2200/PC Make: Rigaku, Japan.
X-Ray: Cu/40 kv/40 mA
Diverging: 10
Scattering Slit: 10
Receiving Slit: 0.15 mm
Monochromator RS: 0.8 mm
Counter: Scintillation Counter
Scan Mode: Continuous
Scan Speed: 3.0000/Min
Sampling Width: 0.020
Scan Axes: Two Theta/Theta
Scan Range: 2.0000 to 40.0000
Theta Offset: 0.0000

In another aspect vilazodone hydrochloride used as the starting material can be prepared by known methods reported in prior art i.e. by using the process as per U.S. Pat. No. 5,532,241.

In another aspect, there are provided pharmaceutical compositions comprising a therapeutically effective amount of amorphous vilazodone hydrochloride substantially free from crystalline form, and one or more pharmaceutically acceptable carriers, excipients or diluents.

The invention also encompasses pharmaceutical compositions comprising vilazodone or salts thereof of the invention. As used herein, the term "pharmaceutical compositions" or "pharmaceutical formulations" include tablets, pills, powders, liquids, suspensions, emulsions, granules, capsules, suppositories, or injection preparations.

Pharmaceutical compositions containing the vilazodone hydrochloride of the invention may be prepared by using diluents or excipients such as fillers, bulking agents, binders, wetting agents, disintegrating agents, surface active agents, and lubricants. Various modes of administration of the pharmaceutical compositions of the invention can be selected depending on the therapeutic purpose, for example tablets, pills, powders, liquids, suspensions, emulsions, granules, capsules, suppositories, or injection preparations.

Having described the invention with reference to certain preferred embodiments, other embodiments will become apparent to one skilled in the art from consideration of the specification.

The process for preparation of amorphous form of vilazodone hydrochloride is demonstrated in examples illustrated below. These examples are illustrative and therefore should not be construed as limitation of the scope of invention.

EXAMPLE-1

Preparation of Amorphous Form of Vilazodone Hydrochloride 25.0 g of vilazodone hydrochloride was dissolved in 250.0 mL of THF-water mixture at 25° C. to 30° C. The mixture was stirred for 30 minutes at 25° C. to 30° C. and 1.0 g charcoal was added and stirred for 30 minutes. The content was filtered through Hyflosupercel, and the Hyflosupercel pad was washed with 50.0 mL acetone. The filtrate was concentrated under vacuum below 45° C. followed by spray drying in JISL Mini Spray Drier LSD-48 under the conditions mentioned below. The product was collected from cyclone and dried at 40° C.±5° C. under vacuum.

| Sr. No | Parameters | Conditions |
|---|---|---|
| a) | Feed pump | 30 rpm |
| b) | Inlet temperature | 60° C. |
| c) | Outlet temperature | 40° C. |
| d) | Aspirator rate | 1300 rpm |
| e) | Vacuum for conveying the dry product | 80 mm of Hg |
| h) | Hot air supply | 2 Kg/cm$^2$ |

The spray-dried vilazodone hydrochloride was amorphous in nature as characterized by X-ray diffraction pattern (FIG. 1).

EXAMPLE-2

Preparation of Amorphous Form of Vilazodone Hydrochloride 10 g of Vilazodone Hydrochloride was dissolved in 125 mL methanol and heated at 65° C. and 100 ml n-heptane was added and stirred for 2-3 hours. The resulting suspension was filtered and dried in air. The obtained solid was amorphous vilazodone hydrochloride having X-ray diffraction pattern as shown in FIG. 1.

EXAMPLE-3

Preparation of Amorphous Form of Vilazodone Hydrochloride 10 g of Vilazodone Hydrochloride (water content of about 10%) was dried in a Fluid Bed Drier at 45° C. for 2 days resulted in amorphous vilazodone hydrochloride having water content less than 5% wt/wt. The obtained amorphous vilazodone hydrochloride was having X-ray diffraction pattern as shown in FIG. 1.

EXAMPLE-4

Preparation of Amorphous Form of Vilazodone Hydrochloride 10 g of Vilazodone Hydrochloride (residual organic solvent of about 10%) was dried in a vacuum tray dryer at about 60° C. under pressure of less than 30 mm/Hg for a period of 24 hours resulted in amorphous vilazodone hydrochloride The obtained amorphous form of vilazodone hydrochloride was having X-ray diffraction pattern as shown in FIG. 1.

While the invention has been described in terms of its specific embodiments, certain modifications and equivalents will be apparent to those skilled in the art and are intended to be included within the scope of the invention.

We claim:

1. An amorphous form of vilazodone hydrochloride comprising the X-ray powder diffraction (XRD) pattern substantially as depicted in FIG. 1.

2. The amorphous form of vilazodone hydrochloride as claimed in claim 1, wherein the vilazodone hydrochloride has the thermal gravimetric analysis (TGA) substantially as depicted in FIG. 2.

3. The amorphous form of vilazodone hydrochloride as claimed in claim 1 having water content of from about 0.5% to about 10% wt/wt.

4. The amorphous form of vilazodone hydrochloride as claimed in claim 1 which is substantially free from residual organic solvents.

5. The amorphous form of vilazodone hydrochloride as claimed in claim 1 having a particle size in terms of d95 less than about 100 microns.

6. A substantially pure amorphous form of vilazodone hydrochloride.

7. The amorphous form of vilazodone hydrochloride as claimed in claim 6 which is substantially free of crystalline forms of vilazodone hydrochloride.

8. The amorphous form of vilazodone hydrochloride as claimed in claim 6 having less than 10% of crystalline vilazodone hydrochloride.

9. The amorphous form of vilazodone hydrochloride as claimed in claim 8 having less than 5% of crystalline vilazodone hydrochloride.

10. The amorphous form of vilazodone hydrochloride as claimed in claim 9 having less than 1% of crystalline vilazodone hydrochloride.

11. A storage stable amorphous form of vilazodone hydrochloride.

12. The stable amorphous form of vilazodone hydrochloride as claimed in claim 11, wherein the amorphous form of vilazodone hydrochloride shows no change in the polymorphic form by X-ray powder diffraction when stored at a temperature of 40° C. and a relative humidity of 75% for a period of at least three months.

13. A process for the preparation of the amorphous form of vilazodone hydrochloride, the process comprising:
(a) providing a solution of vilazodone hydrochloride in one or more solvents; and
(b) recovering the amorphous form of vilazodone hydrochloride from the solution thereof by the removal of the solvent.

14. The process as claimed in claim 13, wherein the solvent comprises one or more of water, alcohols, ketones, esters, hydrocarbons, nitriles, ethers, polar aprotic solvents, or mixtures thereof.

15. The process as claimed in claim 14, wherein the alcohol comprises one or more of methanol, ethanol, isopropanol, 2-propanol, 1-butanol, t-butyl alcohol, 1-pentanol, 2-pentanol, amyl alcohol, ethylene glycol, and glycerol.

16. The process as claimed in claim 14, wherein the ketone comprises one or more of acetone, butanone, 2-pentanone, 3-pentanone, methyl butyl ketone, and methyl isobutyl ketone.

17. The process as claimed in claim 14, wherein the ester comprises one or more of ethyl formate, methyl acetate, ethyl acetate, propyl acetate, t-butyl acetate, and isobutyl acetate.

18. The process as claimed in claim 14, wherein the hydrocarbon comprises one or more of toluene, xylene, methylene dichloride, ethylene dichloride, and chlorobenzene.

19. The process as claimed in claim 14, wherein the ether comprises one or more of diethyl ether, diisopropyl ether, t-butyl methyl ether, dibutyl ether, tetrahydrofuran (THF), 1,4-dioxane, and 2-methoxyethanol.

20. The process as claimed in claim 14, wherein the polar aprotic solvent comprises one or more of N,N-dimethylformamide, N,N-dimethylacetamide, N-methylpyrrolidone, pyridine, dimethylsulfoxide, sulfolane, formamide, acetamide, propanamide, and pyridine.

21. The process as claimed in claim 13, wherein the removing the solvent comprises one or more of distillation, distillation under vacuum, evaporation, spray drying, freeze drying, filtration, decantation, and centrifugation.

22. The process as claimed in claim 13, wherein the vilazodone hydrochloride in an amorphous form is recovered from the solution by spray drying.

23. The process as claimed in claim 13, wherein the vilazodone hydrochloride in an amorphous form is recovered from the solution by freeze drying.

24. A process for the preparation of amorphous form of vilazodone hydrochloride, the process comprising:
(a) providing a solution of vilazodone hydrochloride in one or more solvents;
(b) adding a suitable anti-solvent; and
(c) isolating the amorphous form of vilazodone hydrochloride.

25. The process as claimed in claim 24, wherein the solvent comprises one or more of water, alcohols, ketones, esters, hydrocarbons, nitriles, ethers, polar aprotic solvents, or mixtures thereof.

26. The process as claimed in claim 24, wherein the anti-solvent comprises one or more of hydrocarbons, aromatic hydrocarbons, ethers, or mixtures thereof.

27. The process as claimed in claim 26, wherein the hydrocarbon comprises one or more of hexanes, n-heptane, n-pentane, cyclohexane, and methylcyclohexane.

28. The process as claimed in claim 26, wherein the aromatic hydrocarbon comprises one or more of toluene, xylene, chlorobenzene, and ethylbenzene.

29. The process as claimed in claim 26, wherein the ether comprises one or more of diethyl ether, diisopropyl ether, t-butyl methyl ether, dibutyl ether, tetrahydrofuran, 1,4-dioxane, and 2-methoxyethanol.

30. A process for the preparation of amorphous vilazodone hydrochloride having a particle size in terms of d95 less than about 100 microns, the process comprising:
(a) milling amorphous vilazodone hydrochloride;
(b) slurrying the milled vilazodone hydrochloride in one or more organic solvents to form a solution;
(c) isolating the amorphous vilazodone hydrochloride having particle size in terms of d95 less than about 100 microns.

31. The process as claimed in claim 30, wherein the milling is performed with a feeding pressure of about 3 kg and a grinding pressure of about 4 kg.

32. The process as claimed in claim 30, wherein the solvent comprises is selected one or more of $C_{3-6}$ ketones, water, N-methylpyrrolidone, $C_{3-6}$ amides, halo-substituted $C_{6-12}$ aromatic hydrocarbons, propylene glycol, dimethyl sulfoxide, dimethyl carbonate, $C_{1-8}$ alkyl alcohols, acetonitrile $C_{2-6}$ alkyl acetates, cellosolve, dimethyl carbonate, polyethylene glycol methyl ether and $C_{2-8}$ ethers.

33. The process as claimed in claim 30, wherein the amorphous vilazodone hydrochloride has a polymorphic purity of greater than 99.9% having the X-ray powder diffraction (XRD) pattern substantially as depicted in FIG. 1.

34. A pharmaceutical composition comprising a therapeutically effective amount of an amorphous form of vilazodone hydrochloride and one or more pharmaceutically acceptable carriers, excipients, or diluents.

35. A pharmaceutical composition comprising a therapeutically effective amount of an amorphous form of vilazodone hydrochloride in substantially pure amorphous form having particle size in terms of d95 less than about 100 microns and one or more pharmaceutically acceptable carriers, excipients, or diluents.

36. A method of treatment of major depressive disorders comprising administering a suitable dose of an amorphous form of vilazodone hydrochloride to a subject.

* * * * *